United States Patent
Jo et al.

(10) Patent No.: US 11,459,355 B2
(45) Date of Patent: Oct. 4, 2022

(54) PEPTIDES HAVING OCTOPUS OCTOPRESSIN ACTIVITY AND USE THEREOF

(71) Applicant: NATIONAL MARINE BIODIVERSITY INSTITUTE OF KOREA, Chungcheongnam-do (KR)

(72) Inventors: Seonmi Jo, Gunsan-si (KR); Hye Suck An, Chungcheongnam-do (KR); Seung-Hyun Jung, Gunsan-si (KR); Ha Yeun Song, Gunsan-si (KR)

(73) Assignee: NATIONAL MARINE BIODIVERSITY INSTITUTE OF KOREA, Chungcheongnam-Do (KR)

( * ) Notice: Subject to any disclaimer, the term of this patent is extended or adjusted under 35 U.S.C. 154(b) by 0 days.

(21) Appl. No.: 17/058,528

(22) PCT Filed: Oct. 24, 2018

(86) PCT No.: PCT/KR2018/012636
§ 371 (c)(1),
(2) Date: Nov. 24, 2020

(87) PCT Pub. No.: WO2020/085530
PCT Pub. Date: Apr. 30, 2020

(65) Prior Publication Data
US 2021/0214392 A1  Jul. 15, 2021

(51) Int. Cl.
*C07K 7/06* (2006.01)
*A61K 38/00* (2006.01)

(52) U.S. Cl.
CPC ............... *C07K 7/06* (2013.01); *A61K 38/00* (2013.01)

(58) Field of Classification Search
CPC ................... C07K 7/06; A61K 38/00
See application file for complete search history.

(56) References Cited

FOREIGN PATENT DOCUMENTS

| JP | 2001527537 A | 12/2001 |
| JP | 2003047475 A | 2/2003 |
| KR | 100763938 B1 | 11/2007 |
| WO | 2009009907 A1 | 1/2009 |
| WO | 2016140063 A1 | 9/2016 |

OTHER PUBLICATIONS

Takuwa-Kuroda et al., 2003, Octopus, which owns the most advanced brain in invertebrates, has two members of vasopressin/oxytocin superfamily as in vertebrates, Regulatory Peptides, 115: 139-149.*
Takuwa-Kuroda, K. 等, Octopus, which owns the most advanced brain in invertebrates, has two members of vasopressin/oxytocin superfamily as in vertebrates, Regul. Pept., 2003, 115, 139-149.
NCBI, GenBank Accession No. BAC82435.1, 'octopressin [*Octopus vulgaris*]', Sep. 25, 2003.
Henry, J. 等, 'Identification and expression of two oxytocin/vasopressin related peptides in the cuttlefish *Sepia officinalis*', Peptides, 2013, 46, 159-166.

* cited by examiner

*Primary Examiner* — Amber D Steele
(74) *Attorney, Agent, or Firm* — D'Ambrosio & Menon, PLLC; Usha Menon

(57) ABSTRACT

The present invention relates to an *Octopus minor*-specific octopressin peptide comprising the amino acid sequence of SEQ ID NO: 3, and the peptide, by promoting the brooding behaviors of mother *Octopus minor* to protect her eggs, may increase the hatched larva rate when applied to partial cultivation of octopuses, and thus may be used for the growth of octopus resources.

2 Claims, 5 Drawing Sheets

Specification includes a Sequence Listing.

PEPTIDES HAVING OCTOPUS OCTOPRESSIN ACTIVITY AND USE THEREOF

CROSS REFERENCE TO RELATED APPLICATIONS

This application is a US National Phase entry under U.S.C. 371 of PCT/KR2018/012636, filed on Oct. 24, 2018 by the present inventors, and the contents of which are incorporated by reference herein.

INCORPORATION BY REFERENCE

This application includes a sequence listing in computer readable form (a "txt" file) that is submitted herewith on ASCII text file named PX057395US.ST25.txt, created on Apr. 28, 2022 and 5,050 bytes in size. This sequence listing is incorporated by reference herein.

TECHNICAL FIELD

The present disclosure relates to a peptide having *Octopus minor*-specific octopressin activity and a use thereof

BACKGROUND ART

*Octopus minor* taxonomically belongs to Animalia Cephalopoda Octopoda Octopodidae and mainly inhabits the coasts of Northeast Asia such as Korea, China, and Japan. Since the class Cephalopod to which *Octopus minor* belongs has the most developed brain structure and high intelligence among invertebrates, research development on *Octopus minor* is of great value in the field of neuroscience. Particularly, the mother *Octopus minor* has unique brooding behavior of constantly shaking eggs while not eating food in the mud of the mud flat for about 3 months from spawning to hatching of the eggs. Although *Octopus minor* produces much fewer eggs than octopus, there is a very high possibility of the eggs to grow into full adults.

On one hand, oxytocin is a maternal hormone that not only induces uterine contraction at birth in mammals, but also contracts breast muscles, causing injection of breast milk, making the mother to be sensitive to crying sound of babies, and alleviating stress from caring for babies, such as lack of sleep. Also, oxytocin is a neuropeptide that regulates social behaviors in mammal, regardless of gender, by acting in the brain to trust others and form an attachment relationship. Oxytocin is widely used in pills, injections, and sprays for medical purposes, and it is known that genes similar to oxytocin aid reproductive function in all vertebrates, including humans. Invertebrates do not have oxytocin, but hormones similar to oxytocin are found in some invertebrate species. For example, researches have been published that an oxytocin-like hormone, octopressin, in *Octopus vulgaris* contracts the peripheral tissues of the *Octopus vulgaris* and that another oxytocin-like hormone, cephalotocin, regulates the osmotic resistance in *Octopus ocellatus*. However, there are no studies on maternal behaviors such as spawning and incubating or social-related functions of *Octopus minor*, and particularly, whether or not *Octopus minor* has a gene similar to oxytocin of human or octopressin of *Octopus Vulgaris* has not yet known.

DESCRIPTION OF EMBODIMENTS

Technical Problem

Provided is an *Octopus minor*-specific octopressin peptide consisting of an amino acid sequence of SEQ ID NO: 3.

Provided is a nucleic acid encoding the peptide.

Provided is a recombinant vector including the nucleic acid.

Provided is a composition including the peptide consisting of an amino acid sequence of SEQ ID NO: 3 as an active ingredient.

Provided is a method of promoting brooding behaviors of *Octopus minor*, the method including administering an effective amount of the composition to *Octopus minor* as needed.

Solution to Problem

According to an aspect of the present disclosure, provided is an *Octopus minor*-specific octopressin peptide consisting of an amino acid sequence of SEQ ID NO: 3.

As used herein, the term "octopressin (OTP)" is an oxytocin-like hormone secreted from the *Octopus minor*, and it was confirmed that an oxytocin-like octopressin gene is present in the *Octopus minor* from the results of the genomic analysis of the *Octopus minor* and that the gene promotes a behavior similar to the brooding behavior in an adult *Octopus minor*. In this regard, the peptide not only induces and/or promotes the brooding behavior of the *Octopus minor*, but also promotes copulation of the *Octopus minor* by increasing sociality of the *Octopus minor* regardless of gender. Therefore, when applied to partial cultivation of *Octopus minors*, the peptide may increase the hatched larva rate and thus may be used for the growth of *Octopus minor* resources.

In one embodiment, the peptide may have a disulfide bond formed between amino acids 1 and 6. Also, an amine group ($-NH_2$) may further be bonded to a C-terminal of the peptide. Therefore, the peptide may have activity.

As used herein, the term "peptide" denotes a linear molecule formed amino acids bonded to each other by peptide bonds. The peptide of the present invention may be prepared according to synthetic methods known in the art, for example, a solid-phase synthesis technique. Also, the peptide may include not only the amino acid sequence of SEQ ID NO: 3 described herein but also a biological equivalent thereof. For example, the amino acid sequence may further be modified to improve the brooding behavior, copulation, and/or other biological characteristics of *Octopus minor*. Such modification may include, for example, deletion, insertion, and/or substitution of amino acid residues. These amino acid variation may be made based on the relative similarities, such as hydrophobicity, hydrophilicity, charge, and size, of amino acid side-chain substituents. An analysis of the size, shape, and type of the amino acid side-chain substituents reveals that arginine, lysine, and histidine are all positively charged resides; alanine, glycine, and serine have similar sizes; and phenylalanine, tryptophan, and tyrosine have similar shapes. Therefore, based upon these considerations, arginine, lysine, and histidine; alanine, glycine, and serine; and phenylalanine, tryptophan, and tyrosine may be defined herein as biologically functional equivalents.

To make this change, the hydropathic index of amino acids may be considered. Each amino acid has been assigned a hydropathic index on the basis of their hydrophobicity and charge characteristics: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9);

and arginine (−4.5). The hydropathic amino acid index is important in conferring interactive biological function on a protein. It is known that certain amino acids may be substituted for other amino acids having a similar hydropathic index to retain a similar biological activity. In making changes based upon the hydropathic index, the substitution of amino acids whose hydropathic indices are within ±2 is preferred, those that are within ±1 are particularly preferred, and/or those within ±0.5 are even more particularly preferred.

It is also well known that the substitution between amino acids with similar hydrophilicity values results in proteins having equivalent biological activity. As detailed in U.S. Pat. No. 4,554,101, each amino acid residue has been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Amino acid exchanges in the protein, which do not generally alter the molecular activity, are known in the art (H. Neurath, R. L. Hill, The Proteins, Academic Press, New York, 1979). The most commonly occurring exchanges are changes between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly.

Considering the foregoing mutations with the biological equivalent activity, the peptide of the present invention or a nucleic acid molecule encoding the peptide is construed to also include sequences having substantial identity to the sequences set forth in the sequence listings. The substantial identity means that, when the sequence of the present invention and another optional sequence are aligned to correspond to each other as much as possible and the aligned sequences are analyzed using an algorithm normally used in the art, the corresponding sequences have at least 61%, more preferably at least 70%, still more preferably at least 80%, and most preferably at least 90% sequence identity. Methods of alignment for sequence comparison are known in the art. The NCBI Basic Local Alignment Search Tool (BLAST, Altschul et al., *J. Mol. Biol.* (1990) 215:403-10) is available from the NCBI, and on the Internet, for use in connection with the sequence analysis programs blastp, blasm, blastx, tblastn, and tblastx. BLAST may be accessed at blast.ncbi.nlm.nih.gov. A description of how to determine sequence identity using this program is available at blast.ncbi.nlm.nih.gov.

As used herein, the term "brooding behavior" denotes a behavior of female *Octopus minor* that frequently shakes eggs to hatch the eggs. The *Octopus minor*, a species in the cephalopod class spawns the fewer eggs compared with *Octopus vulgaris* and *Octopus ocellatus*, and the eggs of the *Octopus minor* hatch with special efforts exerted by the mother *Octopus minor* in nursing eggs hiding in the deep cave beneath the mud flat. Embryogenesis in the *Octopus minor*. Kim, Dong-Soo identified author, Kim, Jae-man identified author. Development and Reproduction Vol. 10, No. 2, 2006.10, 135-140) A female *Octopus minor* in the brooding phase, after laying eggs, does unique behaviors including anchoring the eggs on the wall using a green cement secreted from her and frequently shaking the eggs using her arms (legs) and suckers. Also, the female *Octopus minor* continues these behaviors for about 3 months until the eggs hatch, during which the female *Octopus minor* keeps the side of the eggs without eating food. That is, the peptide may increase a hatched larva rate of the *Octopus minor* by promoting the brooding behavior of the *Octopus minor*.

As used herein, the term "social behavior" denotes a behavior of the *Octopus minor*, regardless of gender, that increases sociality of the *Octopus minor* and thus promotes copulation. That is, the *Octopus minors* entering the spawning phase exhibit repetitive behaviors of bending and stretching several arms (legs), approaching other *Octopus minors*, or touching and wiping other *Octopus minors* by stretching the arms (legs), and the male and female *Octopus minors* stay together and engage in social behavior such as mating behavior while crossing the entire arms (legs).

The earthworm, which is an invertebrate, secretes oxytocin-like annetocin, and annetocin, when injected to the earthworm, induces significant behaviors seen at spawning and allows to identify the egg-laying entity as well (J Exp Zool. 1996 Oct. 1; 276(2):151-6. Annetocin, an annelid oxytocin-related peptide, induces egg-laying behavior in the earthworm, *Eisenia foetida*). That is, in vertebrates, oxytocin is involved in childbirth, lactation, and child rearing, and in earthworms, which are invertebrates, oxytocin-like substances may induce mating and spawning. Therefore, the composition may increase a hatched larva rate of the *Octopus minor* by promoting the brooding behavior of the *Octopus minor*, and thus an amount of the *Octopus minor* reproduction may increase.

According to another embodiment, provided is a nucleic acid encoding the peptide. The details of the peptide are the same as described above. In one embodiment, the nucleic acid may include a nucleic acid represented by SEQ ID NO: 1. Also, the nucleic acid may include an open reading frame encoded by an amino acid sequence of SEQ ID NO: 2.

As used herein, the term "nucleic acid" has a meaning that comprehensively includes DNA (gDNA and cDNA) and RNA molecules, and a nucleotide, which is a basic structural unit of the nucleic acid may refer to a nucleotide in the nature as well as a sugar or an analogue with a modified base site. As used herein, sequences of a nucleic acid encoding heavy chain and light chain variable regions may be modified. The modification may include addition, deletion, non-conservative substitution, or conservative substitution of nucleotides.

The nucleic acid of the present invention is construed to also include sequences having substantial identity to the nucleotide sequences. The substantial identity means that, when the nucleotide sequence of the present invention and another optional sequence are aligned to correspond to each other as much as possible and the aligned sequences are analyzed using an algorithm normally used in the art, the corresponding sequences have at least 80%, more preferably at least 90%, and most preferably at least 95% sequence identity.

The DNA encoding the peptide can be easily separated or synthesized using conventional procedures. Many vectors are available. Vector components generally include, but are not limited to, one or more of the following: a signal sequence, an origin of replication, one or more marker genes, an enhancer element, a promoter, and a transcription termination sequence.

According to another embodiment, provided is a recombinant vector including the nucleic acid. The details of the nucleic acid are the same as described above. In one embodiment, the recombinant vector may include primers of SEQ ID NOS: 9 and 10.

As used herein, the term "vector" refers to any vehicle that is used to express a target gene in a host cell, and encompasses: plasmid vectors; cosmid vectors; and viral vectors, such as bacteriophage vectors, adenoviral vectors, retroviral vectors, and adeno-associated viral vectors. In the recombinant vector, the nucleic acid for encoding the antibody is operatively linked to a promoter.

The term "operatively linked" refers to a functional linkage between a nucleic acid expression regulatory sequence (e.g., a promoter, a signal sequence, or an array of transcriptional regulatory factor binding sites) and another nucleic acid sequence, and the regulatory sequence thus regulates the transcription and/or translation of the other nucleic acid sequence.

In cases where the recombinant vector employs a prokaryotic cell as a host cell, it generally includes strong promoters to initiate transcription (e.g., tac promoter, lac promoter, lacUV5 promoter, 1pp promoter, pLλ, promoter, pRλ, promoter, rac5 promoter, amp promoter, recA promoter, SP6 promoter, trp promoter, and T7 promoter), a ribosome binding site for translation initiation, and transcription/translation termination sequences. In cases where the recombinant vector employs an eukaryotic cell as a host cell, the recombinant may employ a promoter derived from the genome of mammalian cells (e.g., metallothionein promoter, β-actin promoter, human hemoglobin promoter, and human muscle creatine promoter) or a promoter derived from mammalian viruses (e.g., adenovirus late promoter, vaccinia virus 7.5K promoter, SV40 promoter, cytomegalovirus (CMV) promoter, tk promoter of HSV, mouse mammary tumor virus (MMTV) promoter, LTR promoter of HIV, promoter of moloney virus, Epstein barr virus (EBV) promoter, and Rous sarcoma virus (RSV) promoter), and may typically have a polyadenylated sequence as the transcription termination sequence. In some embodiments, the recombinant vector may be fused with the other sequences to facilitate the purification of the antibody expressed therefrom. Examples of the fusion sequence include, for example, glutathione S-transferase (Pharmacia, USA), maltose binding protein (NEB, USA), FLAG (IBI, USA), and 6×His (hexahistidine; Quiagen, USA). The vector includes an antibiotic-resistance gene common in the art as a selection marker, which may be, for example, genes resistant to ampicillin, gentamicin, carbenicillin, chloramphenicol, streptomycin, kanamycin, geneticin, neomycin, and tetracycline.

In another aspect, according to another embodiment of the present invention, provided is a cell transformed with the vector described above. The cell used to produce the peptide of the present invention may be, but is not limited to, a prokaryote, yeast, or higher eukaryotic cell. The prokaryotic host cell can be used, for example, a strain belonging to the genus Bacillus such as Escherichia coli, Bacillus subtilis, and Bacillus thuringiensis, Streptomyces, Pseudomonas (for example, Pseudomonas putida), Proteus mirabilis, and Staphylococcus (for example, Staphylococcus carnosus). An example of a useful host cell line having the greatest interest in animal cells may be, but is not limited thereto, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER, C6, SP2/0, NS-0, U205, or HT1080.

According to another embodiment, provided is a composition including a peptide consisting of an amino acid sequence of SEQ ID NO: 3 as an active ingredient. The details of the peptide are the same as described above. According to another embodiment, provided is a method of promoting brooding behaviors of Octopus minor, the method including administering an effective amount of the composition to Octopus minor as needed. The composition may be formulated as animal injections, powders, solutions, granules, or tablets in a manner that may be easily carried out by those skilled in the art. For example, when the composition is prepared as an animal injectable solution or an oral solution, it may be formulated using distilled water, ethyl oleate, ethanol, propylene glycol, or glycerin as a pharmaceutically acceptable carrier. Also, ascorbic acid, sodium hydrogen sulfite, sodium pyruvate, and tocopherol may be used as an antioxidant; and phenyl mercuric nitrate, thimerosal, benzalkonium chloride, phenol, cresol, paraoxymethyl benzoate, and benzyl alcohol may be used as a preservative to formulate the composition. Also, when the composition is prepared as animal powders or granules, vitamins, saccharides such as glucose and lactose, starch, various powders, and liquid enzymes may be formulated in appropriate quantities. Also, the administration of the composition may be carried out by administering to the head or body as an injection, and the composition formulated as a solution may be administered orally or as mixed in drinking water. The composition formulated as powders or granules may be administered in a mixture of drinking water or feed.

In one embodiment, the composition may include a peptide consisting of an amino acid sequence of SEQ ID NO: 3 as an active ingredient to promote brooding behaviors and/or copulation of Octopus minor. The composition may be prepared by adding the peptide within appropriate effective concentration ranges according to various methods known in the art, and an amount of the peptide in the whole composition may be in a range of about 0.01 weight % (wt %) to about 100 wt %, about 0.01 wt % to about 90 wt %, about 0.01 wt % to about 80 wt %, about 0.01 wt % to about 70 wt %, about 0.01 wt % to about 60 wt %, or about 0.01 wt % to about 50 wt %. Also, the composition may be administered repeatedly 1 to 3 times. In particular, the composition may be administered 1 to 3 times, 1 to 2 times, or 2 to 3 times. Here, when the number of administration exceeds these, the Octopus minor may die. The Octopus minor administered with the composition may continue the brooding behavior and/or copulation-promoting behavior for about 5 minutes to about 30 minutes. In particular, the behaviors may continue for about 5 minutes to about 30 minutes, about 5 minutes to about 25 minutes, about 5 minutes to about 20 minutes, about 5 minutes to about 15 minutes, about 5 minutes to about 10 minutes, about 10 minutes to about 20 minutes, or about 10 minutes to about 15 minutes. Also, a duration of the brooding behavior and/or copulation-promoting behavior of the Octopus minor may increase according to the number of administration.

Advantageous Effects of Disclosure

According to an embodiment, an octopressin precursor protein and active peptide is an oxytocin-like hormone secreted from Octopus minor, which promotes brooding behaviors of mother Octopus minor and increases sociality of Octopus minor, regardless of gender, promoting copulation of Octopus minor. Therefore, when applied to partial cultivation of Octopus minors, the peptide may increase the hatched larva rate and thus may be used for the growth of Octopus minor resources.

MODE OF DISCLOSURE

Hereinafter, the present disclosure will be described in more detail with reference to examples. The examples are for only descriptive purposes, and it will be understood by those skilled in the art that the scope of the present disclosure is not construed as being limited to the examples.

EXAMPLE

Example 1. Analysis of Brooding Behavior of Mother *Octopus minor* and Detection of Regulatory Gene 1-1. Analysis of Brooding Behavior of Mother *Octopus minor*

In order to observe brooding behaviors of *Octopus minor*, mother *Octopus minors* were obtained through cooperation with the western branch Resource Creation Department of the Jeonnam Institute of Ocean and Fisheries Science. After purchasing mature individuals (180 to 330 g in weight) collected in April to June 2017 from the sea around Sinan-gun, Jeollanam-do, one female and one male were put into an onion net and then in the natural sea farm in the Resource Creation Department for 1 week to induce copulation, and then only female *Octopus minors* were remained to induce spawning. The clams were fed as food before spawning (once per week), the feeding was stopped after spawning, and the *Octopus minors* were maintained for 1 month or more. Then, the *Octopus minors* were moved to an artificial seawater breeding facility (18° C.) in the resource center for maintenance and observation.

Figure 1:
FIG. 1 shows images of brooding behavior of a mother Octopus minor.

FIG. 1 shows images of brooding behaviors of a mother *Octopus minor*. As shown in FIG. 1, the mother *Octopus minor*, after laying eggs, exhibited unique behaviors including anchoring the eggs on the wall using a green cement secreted from her and frequently shaking the eggs using her arms (legs) and suckers. It was observed that the mother *Octopus minor* continued these behaviors for about 3 months until the fry hatch, during which the female *Octopus minor* kept the side of the eggs without eating food. The *Octopus minor* in nature is known as performing the same spawning brooding behaviors in the deep cave beneath the mud flat, and these behaviors of the mother *Octopus minor* has an effect of cleaning surfaces of the eggs and circulating the surrounding seawater.

1-2. Detection of Regulatory Gene

A full-length genome analysis was performed to identify genes related to the brooding behavior of *Octopus minor*. In particular, after extracting the DNA of the octopus, the full-length genome analysis was performed through next-generation base sequencing techniques (NGS) and bioinformatics methods to obtain a large number of genetic data. Subsequently, the presence of a gene annotated with a gene similar to oxytocin or octopressin of octopus was confirmed by mining the data. From the results, oxytocin-like gene information of about 147 kb in length was obtained, which was named octopressin of *Octopus minor* (Table 1).

TABLE 1

| Scaffold | Shape | Start | End | Transcriptome/protein ID |
|---|---|---|---|---|
| oct000694F | gene | 156,242 | 303,030 | Omin007228 |
| oct000694F | mRNA | 156,242 | 303,030 | Omin007228 |
| oct000694F | exon | 156,242 | 156,317 | Omin007228 |
| oct000694F | CDS | 156,242 | 156,317 | Omin007228 |
| oct000694F | exon | 203,999 | 204,083 | Omin007228 |
| oct000694F | CDS | 203,999 | 204,083 | Omin007228 |
| oct000694F | exon | 231,093 | 231,231 | Omin007228 |
| oct000694F | CDS | 231,093 | 231,231 | Omin007228 |
| oct000694F | exon | 302,349 | 303,030 | Omin007228 |
| oct000694F | CDS | 302,349 | 302,483 | Omin007228 |
| oct000694F | five_prime_UTR | 302,484 | 303,030 | Omin007228 |

Figure 2:
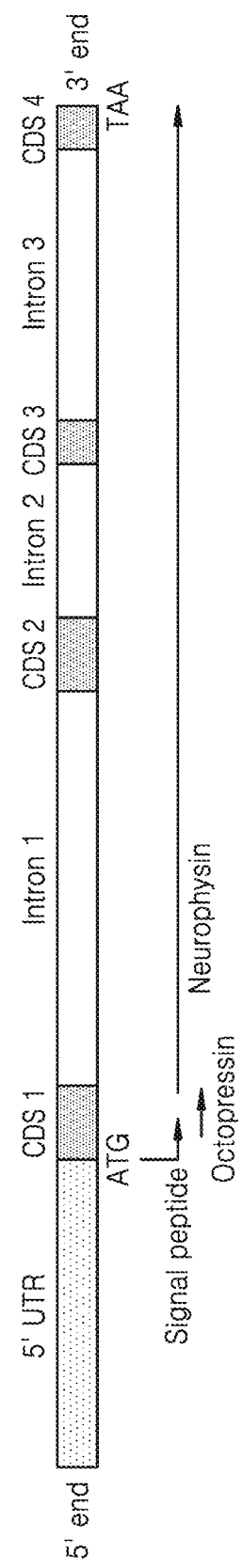
FIG. 2 is a schematic diagram that shows a structure of an octopressin gene in an *Octopus minor* genome (intron size in 1/100 reduction)

FIG. 2 is a diagram analyzing a structure of an octopressin gene in an *Octopus minor*. As shown in FIG. 2, a structure similar to that of an oxytocin gene was confirmed from the full-length nucleotide sequence information of the genome of the octopressin gene.

In addition, from the result of transcriptome analysis, it was confirmed that octopressin mRNA of *Octopus minor* was not expressed at the beginning of development, but the expression level gradually increased as the development process progressed. In particular, it was confirmed that octopressin was expressed more in the brain and intestine in adults, less in the spermatophore, stomach, liver, and mouth, and not in the arms (legs), gills, eyes, heart, kidneys, skin, ovaries, respiratory tract, and poison glands.

In this regard, it was possible to predict that the octopressin of *Octopus minor* may be similar to oxytocin of human. That is, when an expression level of octopressin in a mother *Octopus minor* is significantly increased, it is expected that the octopressin induces brooding behaviors and suppresses the appetite during the period of incubation, and thus this may be applied to the *Octopus minor* partial cultivation and increase a hatched larva rate.

Example 2. Analysis of Regulatory Gene 2-1. Analysis of Coding Nucleic Acid Sequence of Octopressin Gene The coding sequences of octopressin gene predicted by the genome analysis on the *Octopus minor* in Example 1 were analyzed. In particular, the coding nucleic acid sequence (CDS) sites obtained from the genomic analysis result were entered into the ORF finder program (www.ncbi.nlm.nih.gov) of NCBI to obtain a list of possible open reading frames (ORFs). An amino acid sequence of the longest ORF among these was analyzed using the protein blast (blastX) program of NCBI, and thus it was confirmed that the sequence had a part similar to that of other oxytocin-like genes of other species, indicating that it was an octopressin precursor protein.

2-2. Analysis of Octopressin Active Amino Acid Sequence

The amino acid sequence of the active peptide analyzed in Example 2-1 was analyzed, and the amino acid sequence is as follows;

CFWTNCPVG(SEQ ID NO:3).

Particularly, the amino acid sequence was compared with an amino acid sequence of human oxytocin precursor protein, and the similar sites were found and predicted. As a result, the amino acid sequence predicted as an active peptide had a signal peptide in the front part of the amino acid sequence, and a cleavage site and a neurophysin-like site at the end, showing a structure similar to that of the human oxytocin precursor and octopressin of *Octopus vulgaris*. The amino acid sequence of the octopressin active peptide of *Octopus minor* was composed of 9 amino acids, and the two cysteine positions were the same, respectively, and it was confirmed that the amino acid sequence was similar to other oxytocin-based peptides in terms of being terminated with glycine. That is, when the octopressin of *Octopus minor* undergoes amidation, in which a disulfide bond is formed between amino acid 1 (cysteine) and amino acid 6 (cysteine), and $NH_2$ is added at the C-terminal site of amino acid 9 (glycine), the octopressin may act as an active peptide. Also, it was confirmed that the amino acid sequence of the octopressin active peptide of *Octopus minor* was a novel octopressin different from the octopressin amino acid sequence of *Octopus vulgaris* (Table 2).

TABLE 2

| SEQ ID NO: | | | Amino acid sequence | | | | | | | | |
|---|---|---|---|---|---|---|---|---|---|---|---|
| 4 | Homo sapiens | Oxytocin | C | Y | I | Q | N | C | P | L | G |
| 5 | Homo sapiens | Vasopressin | C | Y | P | Q | N | C | P | R | G |
| 6 | Octopus vulgaris | Octopressin | C | F | W | T | S | C | P | I | G |
| 7 | Octopus vulgaris | Cephalotosine | C | Y | F | R | N | C | P | I | G |
| 13 | Octopus minor | Octopressin | C | F | W | T | N | C | P | V | G |
| 8 | Sepia officinalis | Sepiatocin | C | F | W | T | T | C | P | I | G |

Example 3. Synthesis of cDNA of *Octopus minor*-Specific Octopressin Gene and Confirmation of Expression of Octopressin 3-1. Synthesis of cDNA of *Octopus minor*-Specific Octopressin Gene In the spring of 2017, eight female *Octopus minors* (average weight of 183.5 g) caught for the purpose of distribution of seafood on the southwest coast of Korea were purchased and placed in the breeding tank for more than 3 months. Then, the brain of the *Octopus minor* was separated, wrapped in foil, and then rapidly frozen at −70° C. The frozen brain was crushed into a powder using a hammer, put in 3 ml of Isoplus (Takara) solution and dissolved, and RNA was extracted from 1 ml of the mixed solution. Thereafter, cDNA was synthesized from 1 μg of RNA using Super-Script™ IV First strand synthesis system (Invitrogen), and primers were designed to amplify the octopressin gene from the synthesized cDNA (Table 3).

TABLE 3

| SEQ ID NO: | Gene | Nucleic acid sequence |
|---|---|---|
| 9 | Om-S011E-F1 Forward | 5'-GTT TCT GGA CAA ACT GCC-3' |

TABLE 3 -continued

| SEQ ID NO: | Gene | Nucleic acid sequence |
|---|---|---|
| 10 | Om-S011E-R1 Reverse | 5'-GCT GCG ATG ATT CAC TTT GTC-3' |
| 11 | Om-S011C-F1 Forward | 5'-GGA AAT ATT CCC GTG AAA CC-3' |
| 12 | Om-S011C-R1 Reverse | 5'-CAT TTT GCT GAT GAG GGT AG-3' |

3-2. Confirmation of Expression of Octopressin

In order to confirm whether the octopressin gene is expressed in the brain of the *Octopus minor*, RT-PCR was performed on a part of the octopressin gene using the cDNA primers (SEQ ID NOS: 9 and 10) designed in Example 3-1 (5 minutes at 95° C.→(30 seconds at 94° C.→30 seconds at 67° C.→30 seconds at 72° C.)×35 cycles→10 minutes at 72° C.→∞ at 10° C.). Next, the amplified PCR product was electrophoresed on a 1.2% agarose gel to confirm the DNA band.

Figure 3:
FIG. 3 shows the result of amplifying a partial octopressin gene in a brain of *Octopus minor*.

As a result, as shown in FIG. 3, the same band of 317 bp was confirmed in all of the eight *Octopus minors*. Thereafter, in all *Octopus minors*, the coding sequence containing the full-length ORF of the octopressin gene was amplified for cloning.

3-3. Amplification and Confirmation of Coding Sequence Part of Octopressin Gene

In order to obtain the full-length ORF coding sequence of octopressin, the cDNA primers (SEQ ID NOS: 11 and 12) synthesized in Example 3-1 and K-2016 AccuPower PCR premix (Bioneer) were mixed, and RT-PCR was performed on the full-length coding sequence of the octopressin gene (10 minutes at 94° C.→(30 seconds at 94° C.→30 seconds at 60° C.→45 seconds at 72° C.)×30 cycles→10 minutes at 72° C.→∞ at 10° C.). Next, the amplified PCR product was electrophoresed on a 1.2% agarose gel to confirm the DNA band.

Figure 4:
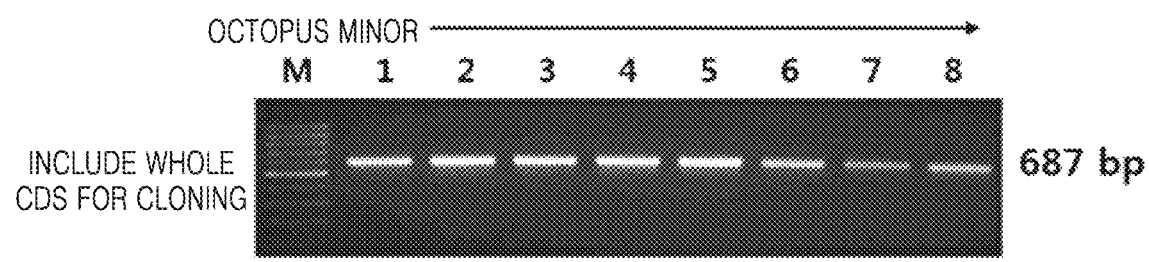
FIG. 4 shows the result of amplifying the whole octopressin gene (including encoding nucleotide sequences) in a brain of *Octopus minor*.

As a result, as shown in FIG. 4, the same band of 687 bp was confirmed in all of the *Octopus minors*. This gene was used in cloning as the octopressin full-length ORF coding sequence was predicted to be included in the gene.

Example 4. Preparation of Recombinant Gene 4-1. Preparation of *Octopus minor*-Derived Recombinant Octopressin Gene In the agarose gel where the PCR product of Example 3-1 was confirmed, the band was cut with a knife while confirming the position of the band with UV. The cut gel was purified using a QIAquick Gel extraction kit (QIAGEN) to purify the amplified DNA contained in the band. The purified PCR product DNA was inserted into the vector using pGEM-T easy vector system I (Promega), transformed into E. coli DH5a competent cells, and cultured in an LB/amp plate. Since the transformed E. coli with the ligation vector grows into white colonies, 5 colonies per Octopus minor were selected and further cultured in LB/amp medium. Then, colony PCR was performed form the same colony (10 minutes at 95° C.→(30 seconds at 94° C.→30 seconds at 55° C.→50 seconds at 72° C.)×30 cycles→5 minutes at 72° C.→∞ at 10° C.) to confirm whether the octopressin ORF coding sequence was properly inserted into the cultured colony. The PCR was performed by adding commercially available sp6 primers and T7 primers. Next, the amplified PCR product was electrophoresed on a 1 agarose gel to confirm the DNA band.

Figure 5:
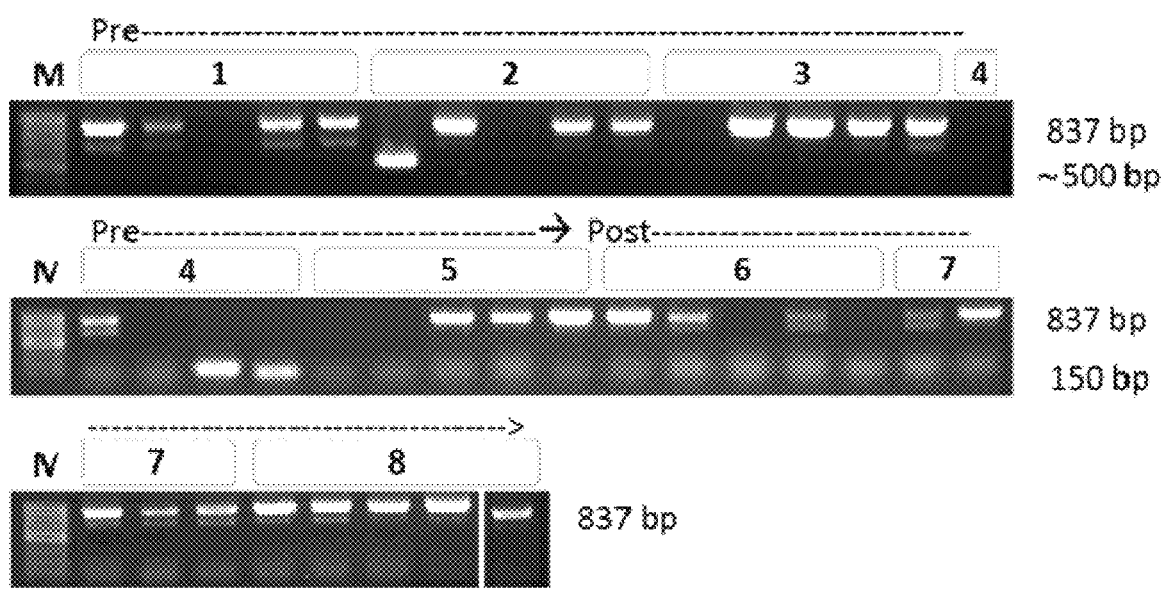
FIG. 5 shows the result of amplifying a part of a cloned vector corresponding to the octopressin gene.

As a result, as shown in FIG. 5, the recombinant plasmid DNA having an octopressin coding sequence inserted in the vector showed the band of 837 bp, and the recombinant plasmid DNA having self-ligated vector showed the band of 150 bp.

4-2. Confirmation of Coding Nucleic Acid Sequence of Recombinant Octopressin Gene Among the E. coli cultured in Example 4-1, 2 colonies exhibiting the band of 837 bp, that are colonies to which the octopressin coding sequence was inserted, were selected per one Octopus minor, and plasmid DNA was extracted therefrom using a QIAprep spin miniprep kit (QIAGEN). Then, the concentration of the extracted DNA was measured, and the nucleic acid sequence was analyzed to confirm inclusion of the octopressin full-length coding sequence, and the nucleic acid sequences predicted in Example 2 were verified. Here, the same primers as those used in Example 2-2 were used, and the nucleic acid sequences were analyzed by Macrogen. Next, the results of the analysis were aligned using the MEGA6 program.

As a result, the nucleic acid sequences of the cloned parts mostly matched the octopressin coding nucleic acid sequences of Example 2-1. Some mutated sequences were also found, but the number of nucleotide sequences in the ORF site was the same in all 8 Octopus minors. Also, the nucleic acid sequences of the cloned parts mostly matched. Some mutated sequences were also found, but the number of nucleotide sequences in the ORF site was the same in all 8 Octopus minors. In addition, it was confirmed that the octopressin active peptide (9 amino acids) and the part corresponding to the signal peptide have the same nucleic acid sequence in all the 8 Octopus minors, and were exactly the same as the sequences predicted through genome analysis in Example 2-2. Although the number of the nucleic acid sequences was the same for the part corresponding to neuropicin and glycopeptides, differences between Octopus minor individuals were found in the nucleic acid sequence, and, diversity of amino acid sequences was confirmed. From these results, it may be confirmed that a recombinant plasmid DNA containing the octopressin full-length coding sequence was successfully prepared from 8 Octopus minors.

Example 5. Analysis of Bioactivity of Octopressin Peptide

Peptides satisfying the octopressin amino acid sequence and modification predicted in Example 4 were ordered and purchased from a peptide synthesizing company and used. A dried peptide powder was dissolved in tertiary distilled water to a concentration of 10 mg/ml, diluted 100 times of artificial seawater filtered through a 0.20 μm filter to prepare an injection solution. A disposable syringe and a 26 gauge needle were used to poke at a 1 cm deep, and the injection solution was administered in the center between the body of the head of the adult Octopus minor. The injection volume was 100 microgram/kg by weight of the Octopus minor. As a control group, Octopus minor without injection (before injection), Octopus minor injected with filtered artificial seawater only, and Octopus minor injected with octopus-derived octopressin were used.

Figure 6A:
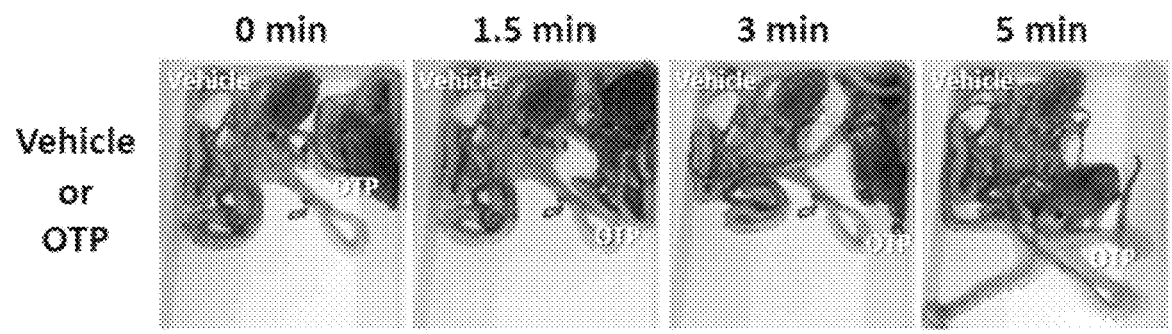
FIG. 6A are images of behavior change of *Octopus minor* after injection of a synthetic peptide that satisfies octopressin amino acid sequence and modification.

FIG. 6A shows images of behavior change in the Octopus minor after injection of the peptide. As shown in FIG. 6A, the Octopus minors exhibited repetitive movements of bending and stretching several arms (legs) were observed, and social behaviors including approaching other Octopus minors, and touching or wiping other Octopus minors by stretching the arms (legs) were induced. In addition, these behavior changes began to appear 1 to 5 minutes after injection and lasted for 10 to 20 minutes, and the effect peaked between 5 to 10 minutes after injection and lasted for 10 to 20 minutes. It was confirmed that the octopressin-activated peptide had bioactivity in 1 to 3 Octopus minors per day, a total of 12 Octopus minors, regardless of sex. Here, the used Octopus minor were discarded without reuse. On the other hand, no specific behavior changes were observed in the Octopus minor without injection at all, the Octopus minor injected with only filtered artificial seawater, and the Octopus minor injected with Octopus minor-derived octopressin.

Figure 6B:
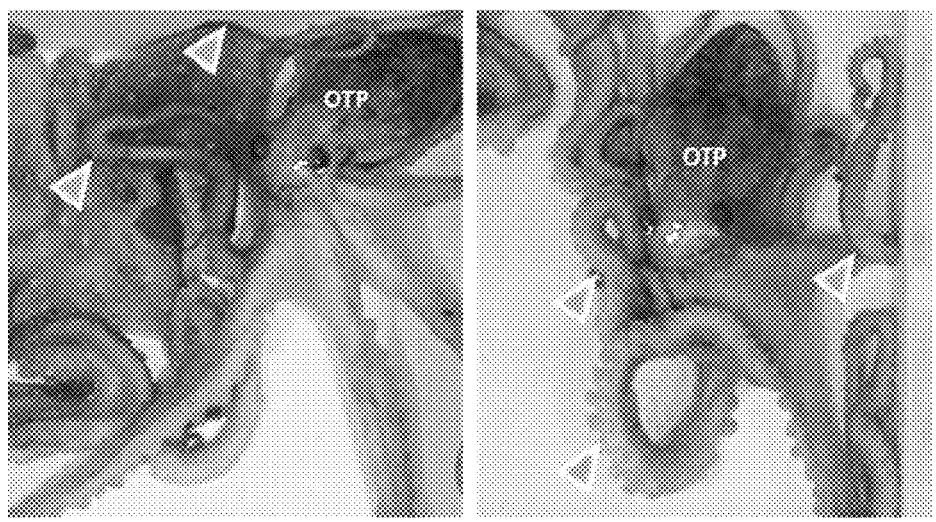
FIG. 6B are images of the *Octopus minor* injected with octopressin showing behavior similar to the brooding behavior.

FIG. 6B shows images of the Octopus minor injected with octopressin exhibiting behaviors similar to the brooding behaviors. As shown in FIG. 6B, since the Octopus minor-derived octopressin may induce the brooding-like behaviors and social behaviors in Octopus minors, when the more Octopus minor eggs are hatched by promoting the copulation, production of Octopus minors may increase, and thus the peptide may be used in the growth of Octopus minor resources.

It will be understood by those skilled in the art that the foregoing description of the present invention is for illustrative purposes only and that those of ordinary skill in the art may readily understand that various changes and modifications may be made without departing from the spirit or essential characteristics of the present invention. Therefore, it should be understood that the embodiments described above are illustrative in all aspects and should not be construed as limiting the scope of the present invention.

The invention claimed is:

1. A method of promoting brooding behaviors of *Octopus minor*, the method comprising administering an effective amount of a composition comprising a peptide consisting of an amino acid sequence of SEQ ID NO: 3 as an active ingredient to *Octopus minor* as needed.

2. The method of claim 1, wherein the brooding behavior lasts for about 5 minutes to about 30 minutes.

* * * * *

SEQUENCE LISTING

```
<160> NUMBER OF SEQ ID NOS: 13

<210> SEQ ID NO 1
<211> LENGTH: 985
<212> TYPE: DNA
<213> ORGANISM: Artificial
<220> FEATURE:
<223> OTHER INFORMATION: Fa162_P1_07228_Octopressin
```

<400> SEQUENCE: 1

```
gagagaagat atctagtagc cgtcagtgtc acacgaagac acctacatta gtaaaaccta      60
gaataaatct agaaaaggct actttgatag atcaaccaat gaaacgagct aactgtgaac     120
taactagcca atcatatatt tgcaaatttt aaaagacaca acaagataaa ccaaagaaga     180
gaaaacaaca aaataaaaca agaaaaataa ccgattaaaa cgagatcaga acctccctaa     240
ccaaatcata ataacgtaa aataatcgaa taaaagttgt acgaaatcta ggctaagtct      300
accgaatttg tgtacaacaa gaaaaataac tacaacgata agaaaaaaaa ccccaaaaaa     360
cccaaaatac tgaagcgaat ttcaaggaaa tattcccgtg aaaccggaaa aaaaagata      420
cggaaccagc aatattaaaa gagctgaata ctaaacaaga gttttaatag aaacacacac     480
atatatacat atatatatat atatataact tgatccccc aaaacttcta aaataaactt      540
agaaaaaatg gcgagtttaa aaagtagtgt ttttgcaatt ttaattgttg tcgtacttct     600
acctattgtg agaagttgtt tctggacaaa ctgccctgtt ggtggcaaaa gaagtaatat     660
acctgcagct gaaccaagaa agtgtatgtc ctgcggaccc aaaggtgaag gccagtgtgt     720
tggacccaac atttgctgcc acaaagacgg ttgtatcata ggcttacttg gaaaagaatg     780
caatgctgaa aacgagagta cgacaccatg ttctgtgaca gctgcctgct cttcgaacac     840
tcgctgtaac accagtggag gccgtagtaa gagtctgaaa gaattacttg cggttctaaa     900
caaaatatgt gacaaagtga atcatcgcag catcgcgatg cagaaattat tggcaatgcg     960
agatggattt tattacaaga aataa                                           985
```

<210> SEQ ID NO 2
<211> LENGTH: 145
<212> TYPE: PRT
<213> ORGANISM: Artificial
<220> FEATURE:
<223> OTHER INFORMATION: Octopressin_ORF2

<400> SEQUENCE: 2

```
Met Ala Ser Leu Lys Ser Ser Val Phe Ala Ile Leu Ile Val Val
1               5                   10                  15

Leu Leu Pro Ile Val Arg Ser Cys Phe Trp Thr Asn Cys Pro Val Gly
            20                  25                  30

Gly Lys Arg Ser Asn Ile Pro Ala Ala Glu Pro Arg Lys Cys Met Ser
        35                  40                  45

Cys Gly Pro Lys Gly Glu Gly Gln Cys Val Gly Pro Asn Ile Cys Cys
    50                  55                  60

His Lys Asp Gly Cys Ile Ile Gly Leu Leu Gly Lys Glu Cys Asn Ala
65                  70                  75                  80

Glu Asn Glu Ser Thr Thr Pro Cys Ser Val Thr Ala Ala Cys Ser Ser
                85                  90                  95

Asn Thr Arg Cys Asn Thr Ser Gly Gly Arg Ser Lys Ser Leu Lys Glu
            100                 105                 110

Leu Leu Ala Val Leu Asn Lys Ile Cys Asp Lys Val Asn His Arg Ser
        115                 120                 125

Ile Ala Met Gln Lys Leu Leu Ala Met Arg Asp Gly Phe Tyr Tyr Lys
    130                 135                 140

Lys
145
```

<210> SEQ ID NO 3

```
<211> LENGTH: 9
<212> TYPE: PRT
<213> ORGANISM: Artificial
<220> FEATURE:
<223> OTHER INFORMATION: Octopressin_active peptide

<400> SEQUENCE: 3

Cys Phe Trp Thr Asn Cys Pro Val Gly
1               5

<210> SEQ ID NO 4
<211> LENGTH: 9
<212> TYPE: PRT
<213> ORGANISM: Artificial
<220> FEATURE:
<223> OTHER INFORMATION: homo sapiens_oxytocin

<400> SEQUENCE: 4

Cys Tyr Ile Gln Asn Cys Pro Leu Gly
1               5

<210> SEQ ID NO 5
<211> LENGTH: 9
<212> TYPE: PRT
<213> ORGANISM: Artificial
<220> FEATURE:
<223> OTHER INFORMATION: homo sapiens_vasopressin

<400> SEQUENCE: 5

Cys Tyr Pro Gln Asn Cys Pro Arg Gly
1               5

<210> SEQ ID NO 6
<211> LENGTH: 9
<212> TYPE: PRT
<213> ORGANISM: Artificial
<220> FEATURE:
<223> OTHER INFORMATION: octopus vulgaris_octopressin

<400> SEQUENCE: 6

Cys Phe Trp Thr Ser Cys Pro Ile Gly
1               5

<210> SEQ ID NO 7
<211> LENGTH: 9
<212> TYPE: PRT
<213> ORGANISM: Artificial
<220> FEATURE:
<223> OTHER INFORMATION: Octopus vulgaris_cephalotocin

<400> SEQUENCE: 7

Cys Tyr Phe Arg Asn Cys Pro Ile Gly
1               5

<210> SEQ ID NO 8
<211> LENGTH: 9
<212> TYPE: PRT
<213> ORGANISM: Artificial
<220> FEATURE:
<223> OTHER INFORMATION: Sepia officinalis_sepiatocin

<400> SEQUENCE: 8

Cys Phe Trp Thr Thr Cys Pro Ile Gly
1               5

<210> SEQ ID NO 9
<211> LENGTH: 21
```

```
<212> TYPE: DNA
<213> ORGANISM: Artificial
<220> FEATURE:
<223> OTHER INFORMATION: Om-S011E-F1

<400> SEQUENCE: 9
gttgtttctg gacaaactgc c                                              21

<210> SEQ ID NO 10
<211> LENGTH: 21
<212> TYPE: DNA
<213> ORGANISM: Artificial
<220> FEATURE:
<223> OTHER INFORMATION: Om-S011E-R1

<400> SEQUENCE: 10
gctgcgatga ttcactttgt c                                              21

<210> SEQ ID NO 11
<211> LENGTH: 20
<212> TYPE: DNA
<213> ORGANISM: Artificial
<220> FEATURE:
<223> OTHER INFORMATION: Om-S011C-F1

<400> SEQUENCE: 11
ggaaatattc ccgtgaaacc                                                20

<210> SEQ ID NO 12
<211> LENGTH: 20
<212> TYPE: DNA
<213> ORGANISM: Artificial
<220> FEATURE:
<223> OTHER INFORMATION: Om-S011C-R1

<400> SEQUENCE: 12
cattttgctg atgagggtag                                                20

<210> SEQ ID NO 13
<211> LENGTH: 9
<212> TYPE: PRT
<213> ORGANISM: Artificial
<220> FEATURE:
<223> OTHER INFORMATION: Octopus minor_Octopressin

<400> SEQUENCE: 13

Cys Phe Trp Thr Asn Cys Pro Val Gly
1               5
```